U
nited States Patent [19]
Schinitsky et al.

[11] Patent Number: 4,938,969
[45] Date of Patent: Jul. 3, 1990

[54] METHOD FOR THE TREATMENT OF AGING OR PHOTO-DAMAGED SKIN

[75] Inventors: Michael R. Schinitsky; Lorraine F. Meisner, both of Madison, Wis.

[73] Assignee: Milor Scientific, Ltd., Madison, Wis.

[21] Appl. No.: 271,213

[22] Filed: Nov. 14, 1988

[51] Int. Cl.$^5$ .................. A61K 33/32; A61K 31/34; A61K 31/195
[52] U.S. Cl. ................................ 424/642; 424/641; 514/474; 514/567; 514/847
[58] Field of Search .................. 514/474, 847, 567; 424/641, 642

[56] References Cited

U.S. PATENT DOCUMENTS

| | | | |
|---|---|---|---|
| 4,668,516 | 5/1987 | Duraffourd et al. | 514/454 |
| 4,704,280 | 11/1987 | Bates | 514/847 |
| 4,743,442 | 5/1988 | Raaf et al. | 514/474 |

OTHER PUBLICATIONS

"Aging-Related Skin Changes: Development and Clinical Meaning", Richey, M. L., Richey, H. K., Fenske, N. A., *Geriatrics*, vol. 43, No. 4, Apr. 1988, pp. 49–61.
"Handbook of The Biology of Aging", Finch & Schneider, eds. 1985, Van Nostrand Reinhold Company, New York, pp. 825–838.
"Topical Tretinoin Improves Photoaged Skin", Weiss, et al., *Jama*, Jan. 22/29, 1988, vol. 259, No. 4, pp. 527–532.
"Oral Zinc Therapy in Geriatric Patients with Selected Skin Manifestations and a Low Plasma Zinc Level", Weismann, et al., *Acta Dermatovener*, 58: 1978, pp. 157–161.

*Primary Examiner*—Douglas W. Robinson
*Assistant Examiner*—Raymond J. Henley, III
*Attorney, Agent, or Firm*—Barnes & Thornburg

[57] ABSTRACT

A composition for reducing the depth or intensity of fine wrinkles in skin affected by intrinsic or photo-induced aging is described. The topical formulation comprises in combination ascorbic acid, tyrosine and a non-toxic zinc salt and is preferably formulated in a hydrophilic ointment or cream base.

2 Claims, No Drawings

METHOD FOR THE TREATMENT OF AGING OR PHOTO-DAMAGED SKIN

BACKGROUND AND SUMMARY OF THE INVENTION

The present invention relates to a composition for improving the appearance of skin affected by natural aging processes and by similar processes accelerated by overexposure to solar radiation. More particularly, this invention relates to a topical formulation which has been found effective to reduce localized furrows (wrinkles) in the epidermis.

Skin is composed of a top layer, the epidermis, which is approximately 20 cell layers or about 0.1mm thick, and a lower layer, the dermis, which is from about 1 to about 4mm thick and contains small blood vessels, collagen, elastin and fibroblasts. The dermis provides structural support and nutrients to the epidermis. While aging has been shown to increase cellular heterogeneity of the epidermal layer, it has little effect on the thickness of that layer. The supporting dermis, however, is known to thin with age and sun exposure. Since the dermal layer provides the support and blood supply for the epidermis, it is of critical importance in maintaining the elasticity and appearance of the skin. Disruption of the supporting dermis layer leads directly to sagging and consequent furrowing of the epidermis, i.e., the formation of wrinkles.

Deep wrinkles are due to continual stretching and contraction of both the dermis and epidermis, and such deep furrows can only be eliminated by plastic surgery or by collagen injections directly beneath the depressed areas. However, fine wrinkles which occur with age (and repeated prolonged exposure to the sun) on skin areas which are less stretched during use are the direct result of deterioration of the supporting dermal layer. Thus during the aging process and in instances where that process has been accelerated by incident radiation, there is disruption of the collagen bundles which collectively provide support to the epidermis.

Collagen exists normally in dense, organized patterns. During the aging process it becomes disorganized and less supportive of the epidermis. Moreover, elastin is lost from the dermis, and there is a progressive loss of circulatory support from the small blood vessels which are more numerous and close to the surface in young skin. The result of aging on skin, whether or not it has been accelerated by incident radiation, is a deterioration of the dermal layer - fewer fibroblasts, less collagen, less elastin and less circulatory support. Consequently, the normal stretching and contraction of the skin leads to damage of the dermis which is not readily corrected and wrinkling results.

Dermatologists and cosmetologists alike have directed their efforts to improving the appearance of skin interrupted by time-telling wrinkles. One much explored approach has been treatment with agents known to stimulate the growth and proliferation of epidermal cells. Because newly proliferated cells provide more structure and hold more moisture, the skin takes on a younger appearance. This has been accomplished by use of an irritant or chemical peel. The uppermost layers of the epidermis are caused to slough off and be replaced with new epidermal cells. While such treatment is recognized to provide some cosmetic improvement, it does not address the major causative factor—the compromised supporting dermal layer.

The present invention is directed to a treatment for sun damaged or aged skin which targets the cells of the supporting dermal layer. We have found that a composition of ascorbic acid, tyrosine and a non-toxic zinc salt, preferably zinc sulfate, in a vehicle suitable for topical application, when applied to areas showing the fine wrinkles associated with aging/sun exposure, results in a readily perceivable diminution of the fine wrinkle structure. While the mode of action of the present composition is not wholly understood, it is believed that the ingredients cooperate to stimulate fibroblast proliferation and to promote their production of collagen and elastin, thereby promoting the supporting role of the associated dermal tissues.

This invention differs from the most prominent current treatment of aged/photo-aged skin, that is, topical treatment with tretinoin (Retin-A). Tretinoin stimulates epidermal cells, but does not result in any observable changes in the dermis [Weiss, JAMA, p. 531 (1988)]. Tretinoin apparently increases epidermal turnover time by stimulating the growth of those cells which are not normally shed as often as younger skin. While the increased proliferation of epidermal cells by tretinoin has been shown to improve the appearance of skin having age-induced wrinkles, it does not compensate for the age-related losses of melanocytes which exist in the epidermis. The increased proliferation of the epidermal cells may lead to more rapid loss of melanocytes and such is known to be associated with increasing susceptibility to sun damage. Therefore, individuals utilizing the tretinoin treatment must take great care to avoid unnecessary exposure to the sun.

DETAILED DESCRIPTION OF THE INVENTION

The present invention is directed to a composition for topical application to reduce epidermal wrinkling resulting from intrinsic aging or photo-aging. The composition comprises from about 2 to about 20%, more preferably about 5 to about 15% ascorbic acid, about 1 to about 10%, more preferably 3 to about 8% tyrosine, and about 0.5 to about 5%, more preferably from about 1 to about 2%, zinc sulfate. Those components are preferably blended into a tissue compatible vehicle, such as hydrophilic lotion-, ointment-, cream- or gel-based vehicle. Such pharmaceutically acceptable vehicles are well known in the art and commercially available for formulation of active ingredients into a suitable form for topical application. Exemplary of such vehicles are the commercially available Dermabase and Unibase formulations.

An essential ingredient in the present composition is a non-toxic, water soluble zinc salt, preferably zinc sulfate. Without zinc sulfate in the present formulation, we have found no beneficial effect. Although it has been observed that aged persons who develop abnormal skin conditions may be deficient in zinc, recent studies suggest that the apparent low serum zinc was actually due to decreased serum albumin, the carrier protein for zinc, and not a zinc deficiency itself. No improvement was noted in patients receiving supplemental zinc, even though elevated plasma zinc was detected.

Initially the present topical preparation was formulated with 3% zinc sulfate and used daily by five female subjects, aged between 45 and 70. One subject discontinued use of the test formulation during the study due to skin irritation. That subject was later maintained on a similar formulation containing only 1% zinc sulfate. All five subjects noted slight improvement in fine wrinkles within a week, particularly those around the mouth. After three months' use, the four subjects who continued participation in the trial, all reported excellent results.

With the success of the Preliminary trial, a double-blind trial was conducted by a cosmetologist. Two formulations were tested. The test formulation was prepared by blending the ingredients shown in Table 1 in the indicated proportions. A control cream was prepared with the same ingredients except without tyrosine and ascorbic acid.

TABLE 1

Formulation for Double-Blind Trial

| Ingredient | % by wt. |
|---|---|
| Mineral Oil | 10.06 |
| Sesame Oil | 2.60 |
| Lanolin | 0.86 |
| Arlacel 165 | 3.47 |
| Atmul 84 | 3.29 |
| Stearic Acid | 0.69 |
| Propyl Paraben | 0.17 |
| $H_2O$ | 58.85 |
| Methyl Paraben | 0.34 |
| Glycerine | 1.04 |
| Propylene Glycol | 1.38 |
| Tyrosine | 5.03 |
| Ascorbic Acid | 10.06 |
| Zinc Sulfate | 2.08 |
| Camomille | q.s. |

One or two independent cosmetologists recorded the location of a fine wrinkle or wrinkle pattern for each of 50 female subjects. Each participant in the study was instructed to utilize the cream sparingly and apply it only to the wrinkled area of the skin to be treated and not to their whole face. The participants were told that the formulation can be applied to the forehead, and the areas around the mouth and chin, but that the area immediately under the eyes should be avoided. The participants were also told that should they experience an uncomfortable tingling or sensation lasting more than a few minutes following application of the cream that they should apply a very light moisturizer cream before application of the test substance. The subjects were also informed that the cream should be applied morning and night.

The subjects were randomly given one of the two cream samples to use twice daily for four weeks. If improvement in the status of the test wrinkle was observed by the subject and the supervising cosmetologist, this was recorded and the subject was not given the other cream sample to test. However, if the first sample given did not yield any improvement, or if there was any irritation associated with its use, the second sample was given to the participant after a one week period for "wash-out". At the end of the four week test for each sample, the wrinkle/wrinkle pattern for each subject was compared with the pattern recorded at the beginning of the trial. After the 50 subjects had used one or both of the cream samples, and their progress, including subjective impressions, had been recorded, the code identifying test cream and control cream was broken. It was learned that 48 out of 50 subjects had noted improvement with the test cream in either the first or second four week test period. One subject reported the test cream ineffective (Her wrinkles were judged by the cosmetologist as being "too deep"), and a second subject found the test sample too irritating and preferred the control cream. This study establishes unequivocably the efficacy of the formulation of the present invention. Further, unlike tretinoin, the benefits of which are lost shortly after discontinuation of use of that drug, the benefits of the composition described herein have been observed to last at least two weeks following discontinued use of the formulation.

We claim:

1. A method of treatment to reduce the depth of wrinkles in a patient's skin affected by intrinsic aging or photo-induced aging, said method comprising the step of applying a composition comprising about 2 to about 20% of ascorbic acid, about 1 to about 10% tyrosine, and about 0.5 to about 5% of a non-toxic zinc salt in a pharmaceutically acceptable carrier, said composition being applied topically to the locus of said wrinkles.

2. The method of claim 1 wherein the composition is applied topically once or twice daily to achieve and maintain dimunition of wrinkle depth.

* * * * *